United States Patent [19]
Shaknovich

[11] Patent Number: 5,807,398
[45] Date of Patent: *Sep. 15, 1998

[54] SHUTTLE STENT DELIVERY CATHETER

[76] Inventor: Alexander Shaknovich, 1349 Lexington Ave., Apt. 7F, New York, N.Y. 10128

[ * ] Notice: This patent issued on a continued prosecution application filed under 37 CFR 1.53(d), and is subject to the twenty year patent term provisions of 35 U.S.C. 154(a)(2).

[21] Appl. No.: 430,378

[22] Filed: Apr. 28, 1995

[51] Int. Cl.$^6$ ........................................... A61F 11/00
[52] U.S. Cl. ..................... 606/108; 606/194; 606/195; 606/198
[58] Field of Search ....................... 606/108, 194, 606/114, 191, 198, 195, 200, 127; 623/1

[56] References Cited

U.S. PATENT DOCUMENTS

| | | | |
|---|---|---|---|
| 3,868,956 | 3/1975 | Alfidi et al. | 606/198 |
| 4,390,599 | 6/1983 | Broyles . | |
| 4,503,599 | 3/1985 | Dotter . | |
| 4,564,014 | 1/1986 | Fogarty et al. . | |
| 4,580,568 | 4/1986 | Gianturco . | |
| 4,655,771 | 4/1987 | Wallsten . | |
| 4,665,918 | 5/1987 | Garza et al. . | |
| 4,688,553 | 8/1987 | Metals . | |
| 4,733,665 | 3/1988 | Palmaz . | |
| 4,739,762 | 4/1988 | Palmaz . | |
| 4,762,128 | 8/1988 | Rosenbluth | 604/96 |
| 4,776,337 | 10/1988 | Palmaz | 623/1 |
| 4,795,458 | 1/1989 | Regan . | |
| 4,817,600 | 4/1989 | Herms et al. | 606/200 |
| 4,830,003 | 5/1989 | Wolff et al. . | |
| 4,886,062 | 12/1989 | Wiktor . | |
| 4,922,905 | 5/1990 | Strecker . | |
| 4,950,227 | 8/1990 | Savin et al. . | |
| 4,950,277 | 8/1990 | Savin et al. | 604/8 |
| 4,969,458 | 11/1990 | Wiktor . | |
| 5,035,706 | 7/1991 | Giantureo . | |
| 5,037,427 | 8/1991 | Harada et al. . | |
| 5,049,132 | 9/1991 | Shaffer et al. | 606/194 |
| 5,059,211 | 10/1991 | Stack et al. . | |
| 5,064,435 | 11/1991 | Porter . | |
| 5,089,005 | 2/1992 | Harada . | |
| 5,089,006 | 2/1992 | Stiles . | |
| 5,102,417 | 4/1992 | Palmaz . | |
| 5,147,370 | 9/1992 | McNamara et al. | 606/108 |
| 5,147,385 | 9/1992 | Beck et al. . | |
| 5,183,085 | 2/1993 | Timmermans . | |
| 5,192,085 | 3/1993 | Hull . | |
| 5,192,297 | 3/1993 | Hull | 606/195 |

(List continued on next page.)

FOREIGN PATENT DOCUMENTS

| | | |
|---|---|---|
| 9409845 | 5/1994 | WIPO . |
| 9526777 | 10/1995 | WIPO . |
| PCT/US95/04146 | 10/1995 | WIPO . |

OTHER PUBLICATIONS

Shaknovich and Schatz, Physician Guide: Palmz–Schatz™ balloon expandable stent for coronary use. ©1994 by Johnson & Johnson Interventional Systems Co.
Fischman et al., 1994, N. Engl. J. Med. 331:496–501.
Serruys et al., 1994, N. Engl. J. Med. 331:489–495.
Topol, 1994, N. Engl. J. Med. 331:539–541.
Dorros et al., 1993, Cathet. Cardiovasc. Diagn. 28:80–82.
Hearn et al., 1993, Circulation 88:2086–2096.
Rocchini et al., 1992, Pediatr. Cardiol. 13:92–96.
Anderson et al., 1992, J. am. Coll. Cardiol. 19:372–381.
Brown et al., 1992 Cathet. Cardiovasc. Diagn. 27:82–85.
Yang et al., 1991, Nippon Acta Radiol. 51:970–972.
Trent et al., 1990, J. Vasc. Surg. 11:707–717.

*Primary Examiner*—Lynne A. Reichard
*Assistant Examiner*—Justine R. Yu

[57] ABSTRACT

The present invention relates to a stent delivery system, including a tubular stent delivery catheter (a "shuttle") comprising an expandable deployment segment, onto which a stent can be mounted in a contracted conformation. Unlike hitherto known delivery catheters, however, the deployment segment is expanded by an ancillary device, for example, by a balloon catheter separate and distinct from the shuttle.

10 Claims, 11 Drawing Sheets

U.S. PATENT DOCUMENTS

| | | |
|---|---|---|
| 5,197,978 | 3/1993 | Hess . |
| 5,201,757 | 4/1993 | Heyn et al. . |
| 5,221,261 | 6/1993 | Termin et al. . |
| 5,224,953 | 7/1993 | Morgentaler . |
| 5,236,447 | 8/1993 | Kubo et al. .................................. 623/1 |
| 5,263,964 | 11/1993 | Purdy ...................................... 606/200 |
| 5,266,073 | 11/1993 | Wall ........................................ 606/194 |
| 5,279,565 | 1/1994 | Klein et al. . |
| 5,282,824 | 2/1994 | Gianturco . |
| 5,304,121 | 4/1994 | Sahatjian . |
| 5,316,023 | 5/1994 | Palmaz et al. . |
| 5,330,500 | 7/1994 | Song . |
| 5,336,178 | 8/1994 | Kaplan et al. . |
| 5,350,397 | 9/1994 | Palermo et al. ......................... 606/200 |
| 5,360,443 | 11/1994 | Barone et al. . |
| 5,364,356 | 11/1994 | Hofling ...................................... 604/96 |
| 5,372,600 | 12/1994 | Beyar et al. ............................ 606/108 |
| 5,389,106 | 2/1995 | Tower . |
| 5,397,307 | 3/1995 | Goodin ...................................... 604/96 |
| 5,458,615 | 10/1995 | Klemm et al. .............................. 623/1 |
| 5,571,086 | 11/1996 | Kaplan et al. ............................. 604/96 |

SHUTTLE STENT DELIVERY CATHETER

INTRODUCTION

The present invention relates to a stent delivery system, including a tubular stent delivery catheter (or "shuttle") comprising an expandable deployment segment, onto which a stent may be mounted in a contracted conformation. Unlike hitherto known delivery catheters, however, the deployment segment is not expanded by means intrinsic to itself, but rather is expanded by ancillary means, for example, by a balloon catheter separate and distinct from the shuttle.

BACKGROUND OF THE INVENTION

Over the past fifteen years, the fields of interventional cardiology and interventional radiology have witnessed a number of paradigm shifts in the treatment of occluded (so called "stenotic") coronary arteries (among other blood vessels), various tubular conduits and similar structures. The earliest approach, still used for particular coronary applications, is by-pass surgery, which constructs a vascular detour around the occlusion. Later, it was found that in certain patients, a much less invasive approach, which did not require thoracotomy, could be used. This technique, known as percutaneous transluminal coronary angioplasty ("PTCA"), introduces a catheter carrying a deflated balloon into a large blood artery in the leg or arm of a patient, threads the catheter into a partially occluded coronary artery, and then inflates the balloon to force open the obstruction. The balloon is then deflated, and the catheter withdrawn from the patient. PTCA has, however, two major shortcomings: first, in 3–5% of patients treated with PTCA, the treated coronary artery re-occludes within the first 24–48 hours after the procedure, despite the use of anticoagulant drugs to deter the reformation of the occlusion (called "abrupt closure"); second, in 30–50% of patients treated with PTCA, the subsequent healing process in the treated coronary artery is associated with sufficient recoil, scarring and/or proliferation of smooth muscle cells to cause re-occlusion of the artery (called "restenosis").

In hopes of preventing abrupt closure and restenosis, coronary artery stents were developed (Topol, 1994, N. Engl. J. Med. 331:539–541). Such stents are tubular devices which provide structural support for maintaining an open vessel. Recently, the placement of such stents has been found to be associated with better angiographic and clinical outcomes than PTCA (Serruys et al., 1994, N. Engl. J. Med. 331:489–495; Fischman et al., 1994, N. Engl. J. Med. 331:496–501), including a lower rate of restenosis. These benefits were achieved, however, at the price of significantly higher procedural costs related to intra- and post-procedural aspects of the stent procedure, and were associated with a significantly higher risk of vascular complications (such as hemorrhage) occurring at the percutaneous access site shortly after the stent procedure. The risk of vascular complications is associated with the aggressive anticoagulation regimen used to avoid thrombosis occurring in the stent itself. Modifications in the strategy of optimal stent placement ("deployment") have been introduced to minimize the risk of such complications.

In order to provide the necessary structural functionality as well as a means for adequate anchoring, stents have been designed which enable the predictable increase or decrease of their radial diameter. Thus, the diameter of a stent may be decreased to permit its introduction into a blood vessel (or similar structure), and then expanded for placement at a desired location. A change in the diameter of such stents may be effected by means integral (self-expanding stents) or ancillary (non-self-expanding stents) to the stent itself.

Self-expanding stents are, prior to placement, maintained in a restrained conformation, such that when the restraints are removed, the stent expands, like a released spring. A stent delivery system for a self-expanding stent typically provides a means for release of the stent after the stent is positioned in the desired location. Patents which disclose examples of such systems include U.S. Pat. No. 4,580,568 (1986) to Gianturco, U.S. Pat. No. 4,655,771 (1987) to Wallsten, and U.S. Pat. No. 4,665,918 (1987) to Garza et al.

Examples of non-self-expanding stents are described in U.S. Pat. No. 4,733,665 by Palmaz, and include, in particular, the Palmaz-Schatz stent, a single slotted tube of surgical grade stainless steel having multiple staggered slots and a central articulation. The staggered slots allow expansion of the inner diameter of the tube, the surface structure of which assumes a configuration resembling chicken-wire as the stent is stretched to wider diameters. For placement, the Palmaz-Schatz stent is typically inserted, disposed upon an inflatable balloon at the tip of a catheter, into a stenotic artery, and the position of the stent is secured by inflating the balloon.

For placement of non-self-expanding stents, a stent delivery system should reliably deliver the stent into a vessel, position the stent in the desired implantation site and maintain the desired position while the stent is radially expanded into the vessel walls. The delivery system must disengage from the implanted stent and allow removal from the vessel in a straightforward manner. For example, U.S. Pat. No. 4,922,905 to Strecker discloses a delivery system for a tubular stent knitted from metal or plastic filament in loosely interlocked loops. This delivery system comprises the stent, compacted onto the balloon portion of a delivery catheter, and a coaxial retractable protective sheath which extends over the stent-balloon assembly. The sheath prevents premature stent expansion and damage to the stent during its passage to and within the vessel. When the stent is positioned in the desired location in the vessel, the protective sheath is retracted and the stent is expanded by applying distending pressure to the balloon. The balloon is then deflated, and the balloon catheter, sheath and the remainder of the delivery system are withdrawn from the vessel. Other patents which disclose examples of such delivery systems include U.S. Pat. No. 4,733,665 (1988) to Palmaz, U.S. Pat. No. 4,950,227 (1990) to Savin et al., and U.S. Pat. No. 4,969,458 (1990) to Wiktor.

Improved strategies, developed prior to the present invention, for implantation of non-self-expanding stents typically incorporate three distinct steps. First, where an obstruction narrows a vessel to an extent which precludes introduction of the stent delivery system, an adequate channel for passage of the balloon-stent assembly is created by inflating a balloon not carrying a stent within the stenosed region (hereafter referred to as predilatation). In order to avoid excessive trauma to the target vessel, the balloon used for pre-dilatation is optimally of slightly smaller diameter than the vessel adjacent to the treatment site. Second, the balloon-stent assembly is advanced into the desired location within the vessel and the stent is expanded by inflating the carrier balloon, so as to achieve contact between the stent and the walls of the vessel (deployment). In order to achieve sufficient expansion of the stent along its entire length and anchoring of the stent in the target vessel, the balloon used for deployment is optimally, when inflated, of the same or slightly greater diameter than the vessel adjacent to the treatment site and of greater length than the stent. Third, optimization of the axially symmetric tubular geometry of the stent and uniform circumferential contact of the stent with the walls of the vessel is achieved by inflating a balloon capable of withstanding high distending pressures within the deployed stent (hereafter referred to as post-dilatation). In order to avoid damage to the target vessel adjacent to the implanted stent, the balloon used for post-dilatation is optimally shorter than the stent. While the first and third of these three steps may occasionally be omitted, they are recommended for most stent placement applications.

For best results, the choice of balloon optimal for one of the foregoing three steps is typically not optimal for the other steps.

The pre-dilatation balloon should have a relatively small uninflated diameter in order to reliably cross into the desired location in the vessel. Further, the pre-dilatation balloon needs to be inflatable to a sufficiently large diameter to create a channel adequate for passage of the stent-balloon assembly.

Because stent deployment systems (developed prior to the invention) for placement of non-self-expanding stents attach the stent to the deployment balloon, such an uninflated stent deployment balloon typically needs to be of larger uninflated diameter relative to the pre-dilatation balloon, so as to permit secure mechanical attachment of the stent, and needs to be longer than the stent itself to insure complete expansion along the entire length of the stent. The deployment balloon needs to maintain its structural integrity during mechanical attachment of the stent and during the delivery of the stent into the target structure. Further, the stent deployment balloon needs to be inflated to pressures sufficient to insure stent expansion and anchoring in the vessel.

The post-dilatation balloon is preferably shorter than the stent in order to minimize trauma to the vessel adjacent to the stent. Moreover, the post-dilatation balloon should be capable of withstanding inflations to high pressures in order to effect optimal and complete stent expansion.

In performing a three-step stent placement procedure, an operator inserting a stent in a patient may typically choose between either using two or more different balloons for the three steps of stent deployment, or using a single balloon for the entire procedure. If multiple balloons are used, the operator may select balloons optimal for each step, at the expense of increased cost of the procedure and additional time required. Balloon exchanges may also require special exchange-length guide wires and additional assistants, may introduce the possibility of loss of access to the treatment site, and typically are associated with some blood loss. If a single balloon is used, optimal performance at one or more of the steps might be compromised. Even if the single balloon strategy is used, the balloon must be removed following pre-dilatation, the stent mounted on it by the operator, and the stent-balloon assembly reintroduced into the patient for stent deployment. As noted above, such manipulations increase the opportunity for hemorrhagic complications and increase the technical difficulty of the stent procedure.

SUMMARY OF THE INVENTION

The present invention relates to a stent delivery system which provides the benefits of an optimal three-step stent placement procedure using multiple balloons, but which obviates the need for balloon exchanges. It is based, at least in part, on the discovery of a tubular stent delivery catheter (hereafter referred to as a "shuttle") comprising a deployment segment having an expandable portion, onto which a stent may be mounted in a contracted conformation. Unlike hitherto known delivery catheters, however, the deployment segment is not expanded by means intrinsic to itself, but rather is expanded by ancillary means, for example, by a balloon catheter separate and distinct from the shuttle. Multiple balloon changes are rendered unnecessary because the structural design of the deployment segment supplies the optimal physical characteristics offered by multiple balloons.

For example, in a particular embodiment of the invention, a shuttle comprises a deployment segment having an expandable portion over which a stent is mounted in contracted condition. The stent-bearing expandable portion of the deployment segment is flanked by segments which are not expandable to the same degree as the stent-bearing portion. Optionally, the deployment segment comprises a releasable biological, pharmaceutical, or structural substance. For stent placement in a partially occluded blood vessel (or similar structure) in a patient, a guide wire, having a length greater than the balloon catheter, may be introduced into the vessel. A shuttle with an expandable stent mechanically or by other means attached onto the deployment segment in contracted condition, may be mounted coaxially over the shaft of the balloon catheter outside the patient. The shuttle may be designed to be coaxially mounted over the shaft of the balloon catheter over the entire length of the shuttle (hereafter referred to as an "over the catheter" shuttle) or only over a distal segment of the shuttle comprising the deployment segment (hereafter referred to as a "monorail" shuttle). For the over-the catheter shuttle, the balloon catheter used has a length greater than the shuttle. The balloon catheter is designed such that the balloon is reliably and repeatedly capable of advancing in unexpanded (i.e., never inflated) or collapsed (i.e., inflated at least once and then deflated) condition through the entire length of the shuttle and in and out of the distal end of the stent shuttle. The occluded region of the vessel may then be pre-dilated using the balloon catheter. Then, without withdrawing the balloon catheter from the patient, the balloon may be deflated and advanced beyond (distal to) the occlusion, and the shuttle, fitting over the shaft of the balloon catheter, may be positioned such that the stent-bearing deployment segment is positioned within the predilated occluded portion of the vessel. The balloon may then be pulled back into the deployment segment of the shuttle, and expanded to high pressures. Expanding the balloon accomplishes deployment of the stent, and also offers the benefits of post-dilatation. The need for a separate, shorter, post-dilatation balloon should be obviated by the relatively non-expandable segments flanking the expandable region of the deployment segment, which protect the vessel adjacent to the stent from damage. Moreover, releasable substances comprised in the deployment segment may be liberated by the expansion of the deployment segment via inflation of the balloon. Following stent deployment, the balloon may be deflated and the stent delivery and balloon catheters may be removed from the patient.

In various embodiments, the stent delivery system of the invention may be used for the placement of either non-self-expanding or self-expanding stents in blood vessels or similar structures.

The present invention further provides for embodiments which enable the placement of multiple stents in a single procedure, as well as for embodiments incorporating a means for trapping material dislodged in the stent placement process, thereby diminishing the risk of distal embolization.

DETAILED DESCRIPTION OF THE INVENTION

Stent delivery systems of the invention share the common feature of a shuttle having a stent deployment segment which is expanded by a means ancillary to the delivery catheter, such as by a balloon catheter.

Such systems may be better understood by reference to the figures, which illustrate nonlimiting embodiments of the invention.

Figure 1:
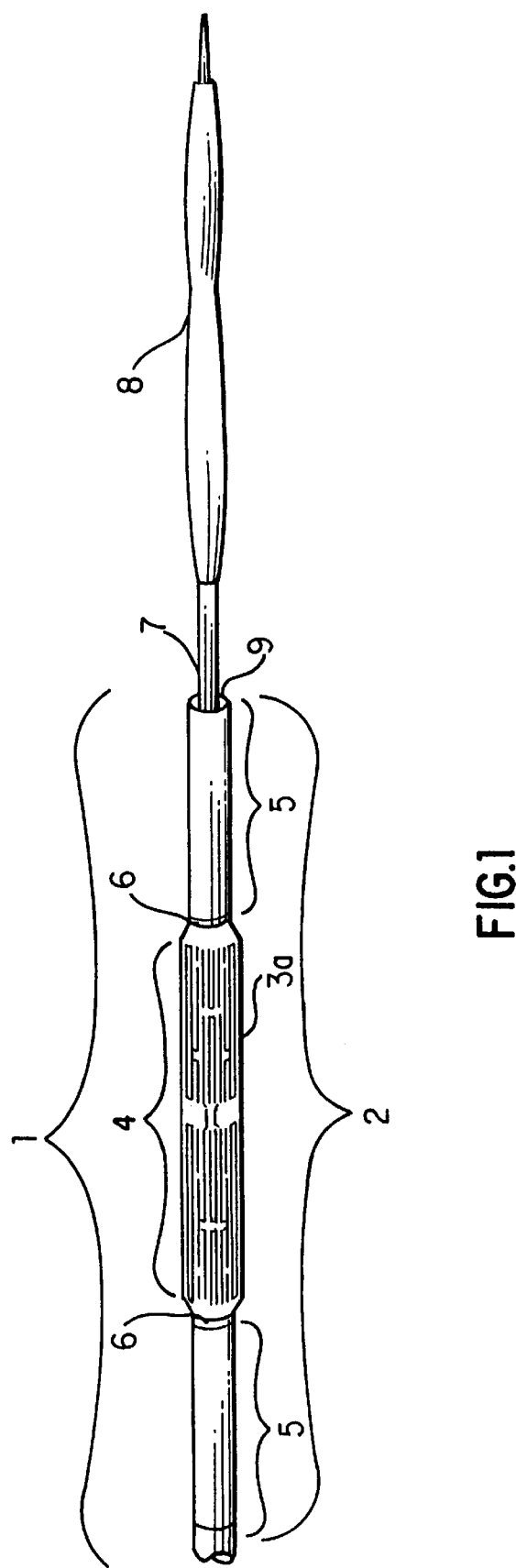
FIG. 1. The distal end of a stent delivery system according to the invention.

FIG. 1 depicts the distal end of a stent delivery system according to the invention, comprising a shuttle (1) having a deployment segment (2) carrying a stent (here, a non-self-expandable Palmaz-Schatz stent; 3a) compacted over an expandable portion (4) of the deployment segment, which is flanked by relatively non-expandable segments (5). Detectable markers (6) are located on the expandable portion of the deployment segment, which may be used to monitor the position of the stent. The shuttle in this embodiment is coaxial with the shaft of a balloon catheter (7), here showing the balloon (8), in an uninflated condition, extending beyond the distal end (9) of the shuttle.

Figure 2:
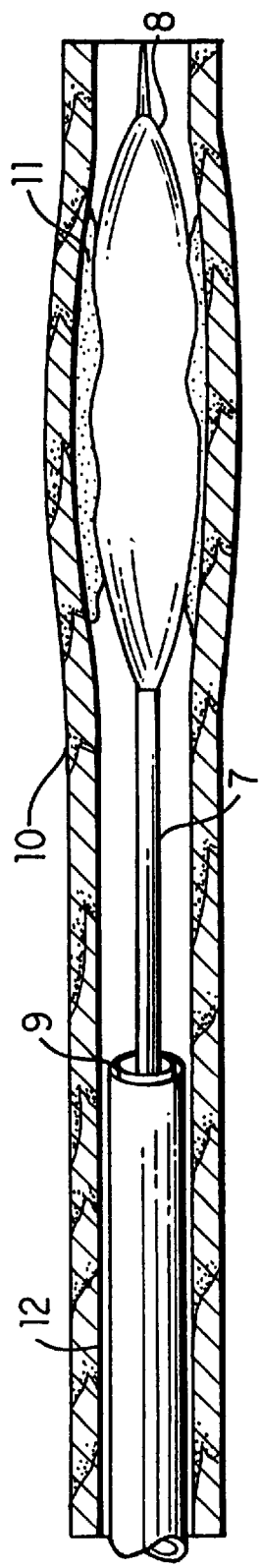
FIG. 2. Pre-dilatation of a partially occluded vessel.

FIG. 2 presents a diagram of pre-dilatation of a partially occluded vessel (10), prior to stent placement, using the system depicted in FIG. 1. The balloon (8) has been passed, in an uninflated condition, within the occluded area (11) and then inflated. The shuttle remains in the guiding catheter (12).

Figure 3:
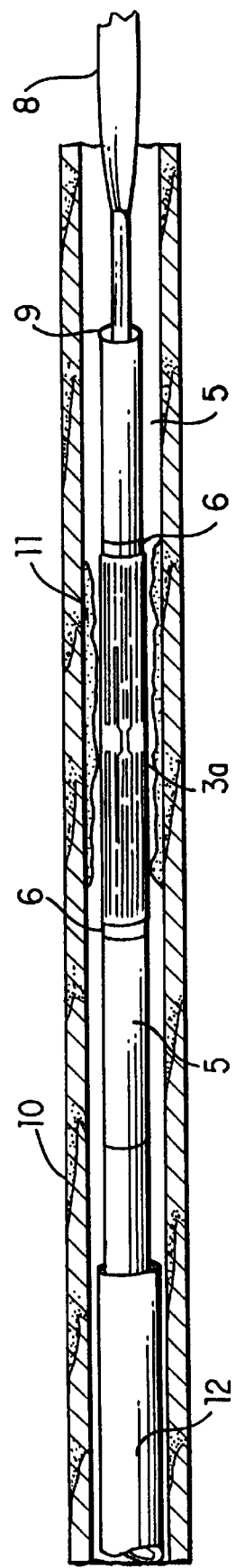
FIG. 3. Stent positioning following predilatation.

FIG. 3 presents a diagram of stent positioning following pre-dilatation as shown in FIG. 2. The balloon (8) has been deflated and advanced beyond (distal to) the pre-dilated occluded region of the vessel (11), and the deployment segment of the shuttle has been advanced over the shaft of the balloon catheter such that the stent (3a) is in the desired position, as indicated by the detectable markers (6).

Figure 4:
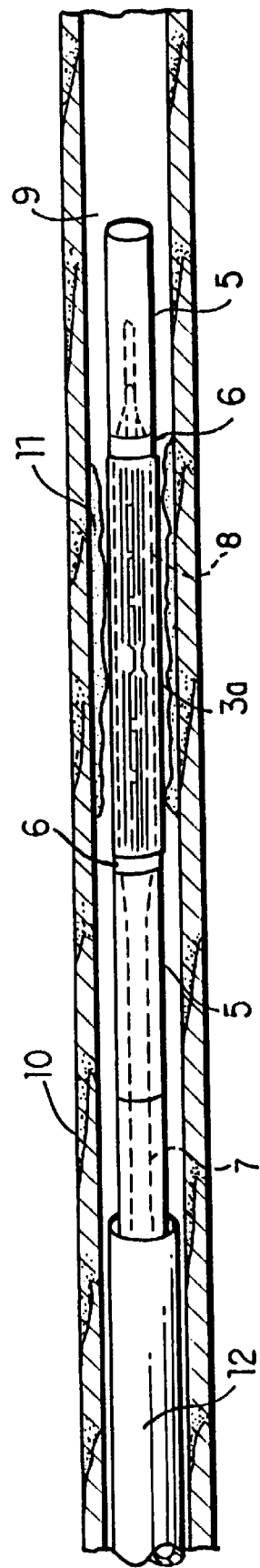
FIG. 4. Withdrawal of the balloon into the deployment segment.

FIG. 4 presents a diagram of preparation for stent deployment following proper positioning of the stent as shown in FIG. 3. Keeping the distal end (9) of the shuttle stationary, the deflated balloon (8) has been pulled back into the deployment segment of the shuttle.

Figure 5:
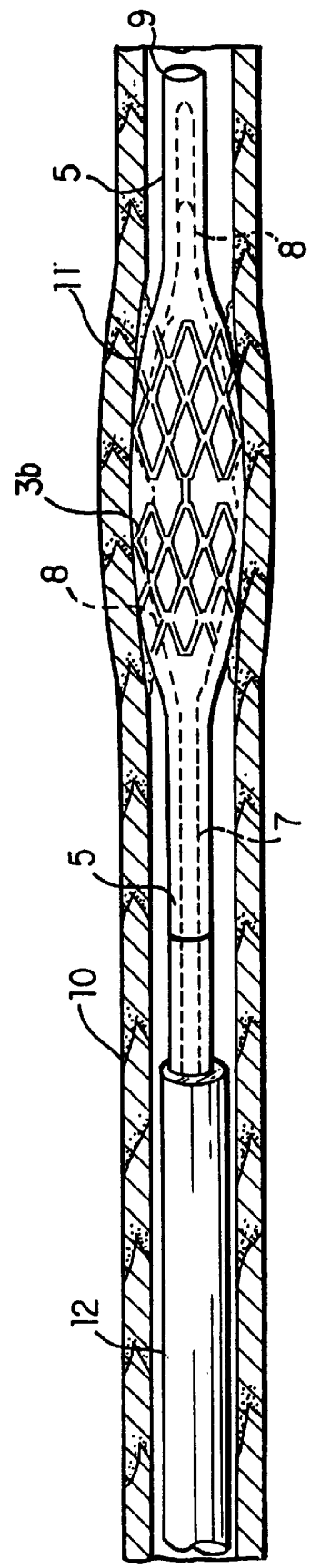
FIG. 5. Stent deployment.

FIG. 5 presents a diagram of stent deployment following repositioning of the balloon as shown in FIG. 4. The balloon (8) is inflated to effect deployment of the stent, (which assumes an expanded conformation; 3b). Note that the regions of the deployment segment (5) flanking the expandable portion (4) do not expand to the same degree as the stent-bearing expandable portion (4), thereby sparing the vessel (10) adjacent to the stent from damage.

Figure 6:
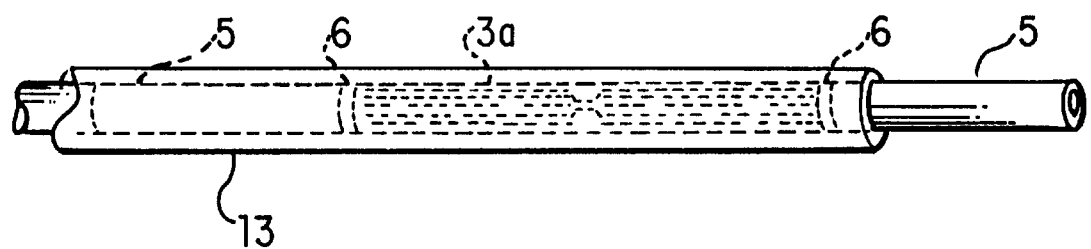
FIG. 6. Protective sheath extending over the stent.

FIG. 6 depicts a protective sheath (13) which originates proximally and extends over the stent (3a).

Figure 7:
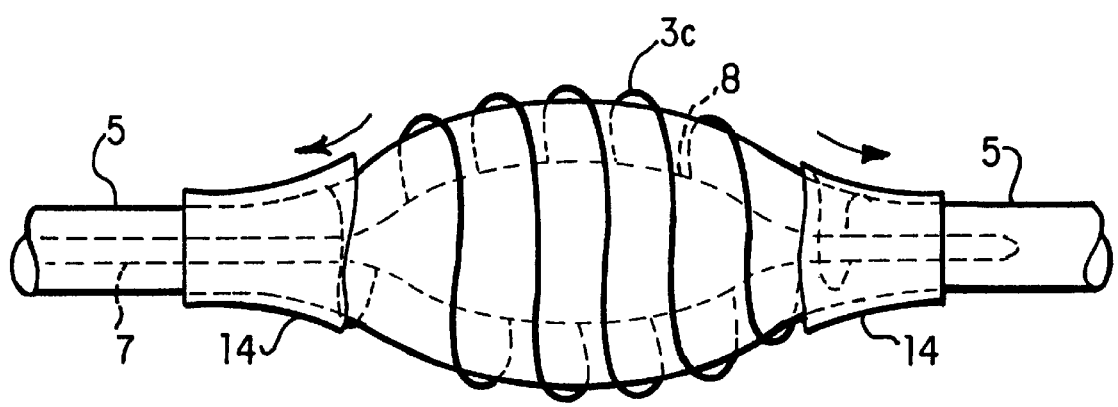
FIG. 7. Release mechanism of self-expanding stent.

FIG. 7 depicts a release mechanism for a self-expanding stent (3c), wherein the stent (3c) is restrained, prior to deployment, by sleeves (14) which are attached to the flanks (5) of the deployment segment (2), wherein the sleeves (14) are pulled apart (as shown by arrows) when the deployment segment (2) is expanded by a balloon (8). By pulling apart the sleeves (14), the stent (3c) is released and allowed to expand.

Figure 8:
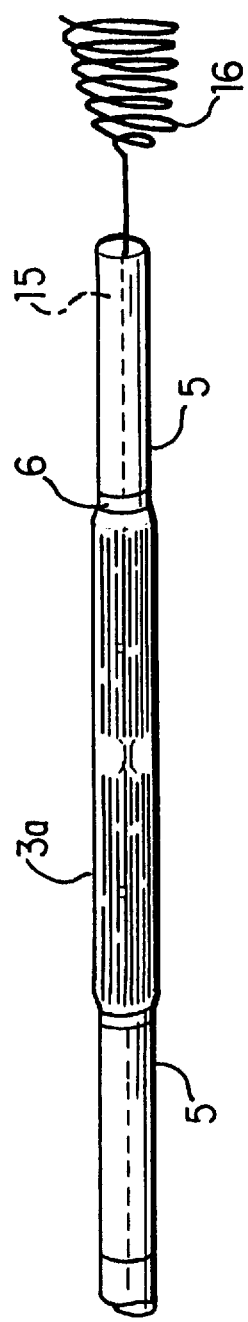
FIG. 8. Embolic filter at distal end of shuttle.

FIG. 8 depicts an embolic filter (16) attached to a thin shaft (15) running through the inner lumen of the shuttle; The shaft (15) may be manipulated by the operator at the proximal end of the shuttle, and may be used to advance, retain, or withdraw the embolic filter.

Figure 9:
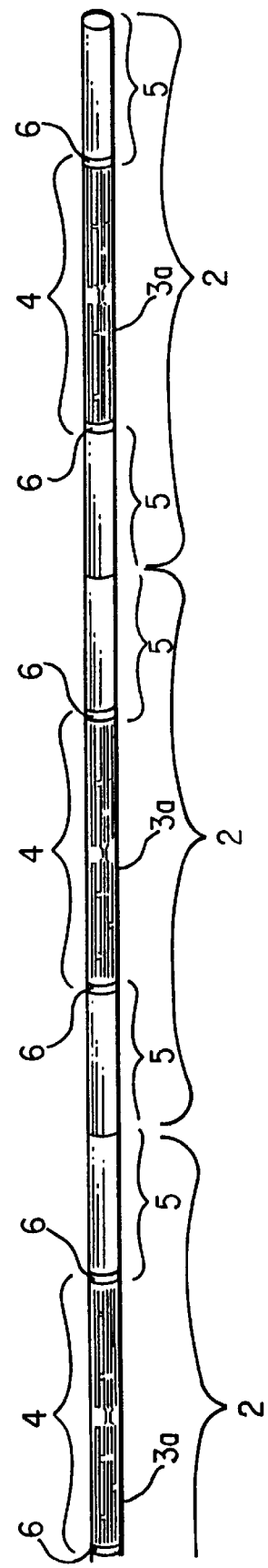
FIG. 9. Distal end of shuttle for multiple stent deployment.

FIG. 9 depicts the distal end of a shuttle used to deploy multiple stents (3a), showing multiple deployment segments (2).

Figure 10:
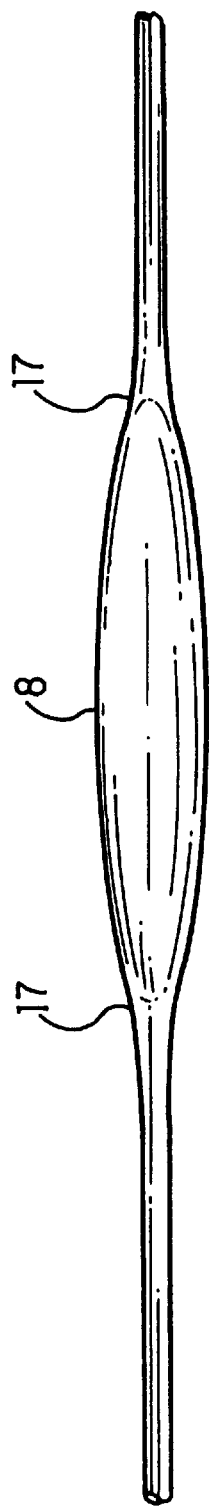
FIG. 10. Balloon design, showing long tapered ends and small refolded diameter.

FIG. 10 depicts a balloon (8), showing long tapered ends (17) and small refolded diameters.

Figure 11A:
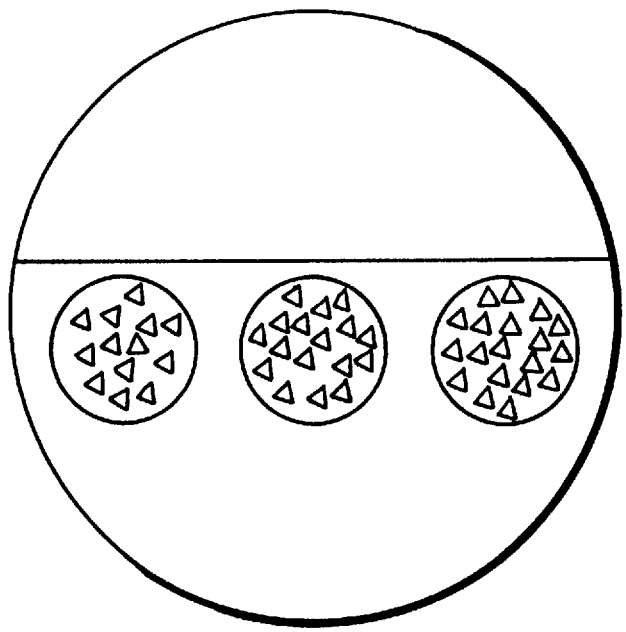
FIG. 11. (A/B) Release of a pharmaceutical substance during stent deployment.
Figure 11B:
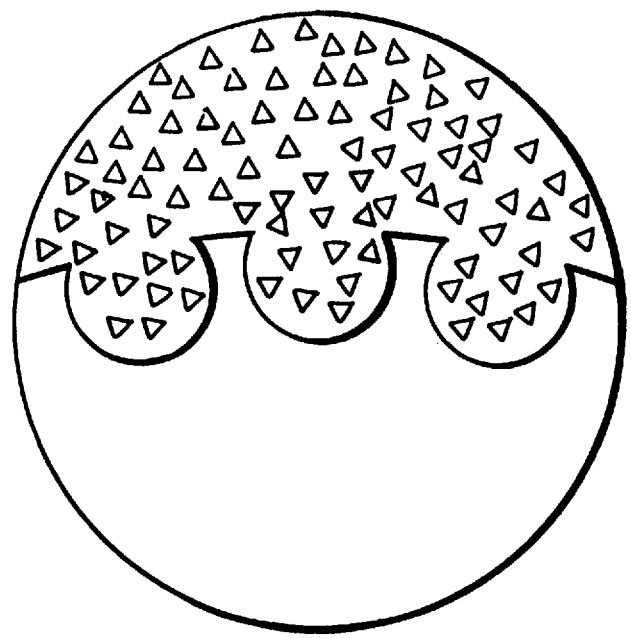

In FIG. 11, a pharmaceutical substance (magnified cross-sectional views; pharmaceutical substance represented by open triangles) comprised in thin walled vacuoles in the deployment segment (A) is released when the deployment segment is expanded, causing the vacuoles to rupture (B).

For purposes of clarity of description, and not by way of limitation, a further detailed description of the invention is divided into the following subsections:

(i) stents;

(ii) shuttles;

(iii) ancillary means of expansion; and (iv) methods of stent placement.

STENTS

Stents which may be delivered according to the invention include any stent intended to be placed within a blood vessel (e.g. an artery or vein, including but not limited to a coronary artery, a carotid artery, the aorta and vena cava) or similar structure. Similar structures include, but are not limited to, tubular organs or spaces such as a ureter, urethra, esophagus, bile duct, tear duct, bronchus or trachea.

Vascular stents which may be used according to the invention include but are not limited to Palmaz-Schatz, Gianturco-Roubin, Strecker, Wiktor, Wallsten and Cordis stents. Stents which may be delivered according to the invention are not limited as to the design, material, length or thickness of the stent, and multiple contiguous or non-contiguous stents may be delivered.

SHUTTLES

A shuttle, according to the invention, is a tubular structure having a distal and a proximal end, wherein the proximal end may preferably be kept outside of the patient (thereby allowing the operator to adjust the position of the stent during placement) and comprising a deployment segment (used for carrying and deploying the stent) located at or near the distal end. A specific example of the distal end of such a shuttle is depicted in FIG. 1.

The shuttle may be fabricated from a variety of materials, including, but not limited to, polyethylene, nylon, and nitinol, which are the preferred materials for the placement of stents in blood vessels. The length and radial diameter of the shuttle may vary depending upon the vessel or similar structure into which the stent is to be placed. For example, the approximate length of the shuttle for placement of a stent into a coronary artery may be in the range of from 80 to 140 centimeters, and preferably from 90 to 125 centimeters, the outer radial diameter may be in the range of from 1.0 to 2.0 millimeters, and preferably from 1.3 to 1.7 millimeters, and the inner radial diameter may be in the range of from 0.8 to 1.6 millimeters, and preferably from 0.9 to 1.3 millimeters.

The deployment segment of the shuttle comprises an expandable portion, onto which the stent may be mounted (e.g., compacted) prior to placement in a patient, and regions flanking the expandable portion (called "flanks") which are not expandable or are less expandable than the expandable portion. The expandable portion and flanks may be fabricated of different materials, having different expandabilities. Alternatively, the expandable portion may be made of the same material as the remainder of the shuttle, and the flanks may be created by placing two short tubular portions of reinforcing material at the distal end of the delivery catheter, with a space between the short tubular portions, wherein the space is the expandable portion of the deployment segment. For example, for purposes of placing a stent in a coronary artery, the length of the expandable portion may be as long as, or preferably only slightly longer than, the stent which is to be placed, for example, in the range of from 5 to 35 millimeters, and preferably from 9 to 30 millimeters. Markers, for example radiopaque markers such as gold, tantalum or platinum markers may be placed at the boundaries between the expandable portion and the flanks or between the flanks and the remainder of the shuttle to aid in stent positioning.

The stent may be compacted onto the expandable portion of the deployment segment prior to placement in the patient. For non-self-expanding stents, such as, for example, a Palmaz-Schatz stent, the stent may simply be crimped onto the expandable portion of the deployment segment. For self-expanding stents, the stent may be retained in non-expanded form on the shuttle by a restraining mechanism. For example, constraining sleeves may extend over both edges of the stent, retaining it in place until the sleeves are pulled apart by expansion of the expandable portion of the deployment segment (see, for example, FIG. 7). In the case of self-expanding or non-self expanding stents, the shuttle may optionally comprise a protective sheath which may cover the stent prior to deployment (see, for example, FIG. 6); such a sheath may be removed by retracting it by pulling on its proximal end, which may be kept outside of the patient at all times.

In nonlimiting embodiments of the invention, more than one deployment segment/stent assembly may be comprised in a single shuttle, so as to permit the placement of multiple stents during a single procedure (see, for example, FIG. 9).

In certain, nonlimiting embodiments of the invention, biological, pharmaceutical, and/or structural materials may be incorporated into the deployment segment of the shuttle, such that these materials may be released upon expansion of the deployment segment by an ancillary means. For example, such materials may be incorporated into thin-walled vacuoles near the surface of the deployment segment closest to the wall of the vessel or similar structure into which the stent is to be placed, such that the vacuoles may rupture, releasing their contents, when the deployment segment is expanded. As another example, a biodegradable polymer layer with antithrombotic and/or antiproliferative properties may be incorporated into the stent delivery catheter either over the mounted stent or between the stent and the expandable portion of the deployment segment. When the deployment segment and the stent are expanded, this layer may be released from the shuttle while remaining attached to the stent in the treatment site. Materials which may be incorporated into the deployment segment include, but are not limited to, anticoagulants such as heparin, hirudin, hirulog, or platelet receptor inhibitors, thrombolytic agents such as tissue plasminogen activator, compounds that deter the proliferation of vascular smooth muscle cells (thereby decreasing the likelihood of restenosis) such as radioactive compounds, anti-CD41 antibodies or antisense oligodeoxynucleotides, radiopaque materials such as iodine or barium salts, structural materials such as fibrin layers, endothelial cells, segments of veins or arteries or synthetic grafts such as dacron. It should be noted that incorporation of such materials into the deployment segment, with consequent local release at the site of stent placement, may decrease or eliminate the need for systemic administration of such agents or other adjunct therapies. For example, the need for aggressive systemic anticoagulation may be decreased, thereby diminishing the likelihood of hemorrhagic complications at the vascular access site.

In particular, nonlimiting embodiments of the invention, the distal tip of the shuttle may be designed so as to facilitate withdrawal of an ancillary means of expansion such as a balloon into the deployment segment, for example subsequent to pre-dilatation. In alternative embodiments, the distal end of the shuttle may be either of a fixed or of an alterable configuration. For example, to achieve an alterable configuration, the distal tip of the shuttle may be constructed of a thermal memory alloy, such as nitinol. Such a nitinol tip may be maintained at a small radial diameter to facilitate passage of the catheter into a vessel or similar structure. Following pre-dilatation, for example with a balloon catheter, when it is necessary to withdraw the deflated balloon into the deployment segment of the shuttle, the configuration of the nitinol tip may be altered, for example, using a weak electrical current, to assume a funnel shape that may better accommodate withdrawal of the balloon. Termination of the current may then restore the initial shape of the distal tip of the shuttle.

In further nonlimiting embodiments of the invention, the shuttle may comprise, at its distal end, a structure capable of forming an embolic filter, with fenestrations large enough to permit the passage of blood or other fluid, but small enough to trap debris (such as fragments of thrombus or atherosclerotic plaque) freed during predilatation or stent deployment. The filter may be capable of fitting over, for example, a balloon catheter shaft or guidewire, and may be capable of expansion by intrinsic or ancillary means. For example, an intrinsic means of expansion would include a filter constructed of a thermal memory alloy such as nitinol, which may be expanded by a weak electrical current. As an example of an ancillary means of expansion, a balloon may be used to expand the filter. In either case, the filter and distal region of the shuttle may desirably be constructed such that the filter may be advanced distal to the obstructed region of the vessel and expanded prior to pre-dilatation and stent deployment. The filter itself may preferably be sufficiently flexible, by virtue of the material of which it is made or its construction, to permit pull-back of the entire delivery system following stent deployment, with the filter in its expanded shape.

A non-limiting example of such an embolic filter, comprised at the distal end of a stent delivery sheath, is depicted in FIG. 8. According to this embodiment, the filter is comprised in a separate element, wherein the filter (including, but not limited to, a coiled structure as depicted in FIG. 8) is positioned distal to the distal end of the shuttle, and is connected to a small diameter shaft running through the shuttle and extending its proximal end outside of the patient, to permit manipulation by the operator (e.g. forward advancement, retention, and withdrawal). Such a filter may be particularly useful, for example, in the placement of a carotid artery stent, to diminish the risk of embolization of thrombus or plaque to the brain, which may have profound clinical consequences and has, hitherto, limited the applicability of the stent-based treatment strategy in cerebral vasculature. For placement in a partially obstructed carotid artery, for example, the shuttle with an expandable filter at its distal tip and with the stent attached in a compacted condition over the expandable deployment segment of the shuttle may be coaxially mounted over the shaft of an appropriate balloon catheter outside the patient. The unexpanded balloon may be advanced over a guidewire distal to the lesion while the shuttle is retained inside the guiding catheter. Then, using the small diameter shaft, the embolic filter may be separated from the remainder of the shuttle and advanced over the shaft of the balloon to a position distal to the obstruction. The filter may then be expanded by intrinsic or ancillary means (e.g., the balloon), wherein the expanded filter may protect the brain from embolization during pre-dilatation of the treatment site and during stent deployment. While keeping the embolic filter stationary, the obstructed segment may then be pre-dilated with the balloon. The balloon may then be deflated and advanced over the guide wire distal to the treatment site. Maintaining the embolic filter in its location, the shuttle may then be positioned so that the expandable segment with the stent mounted on it is in the desired location. While the positions of the shuttle and the filter are maintained, the balloon catheter may then be pulled back into the expandable segment and inflated, thereby deploying the stent. Following balloon deflation, the shuttle-balloon catheter assembly with the filter in its expanded conformation may be pulled out of the carotid artery into the descending aorta and out of the patient. Relatively small fragments of plaque and/or thrombus released during the procedure and trapped in the filter may thus be removed out of the patient or may embolize into the systemic arterial circulation with much less grave clinical sequelae.

In an additional, non-limiting embodiment of the invention, the embolic filter may have an alterable configuration; for example, the filter may be constructed of nitinol, and have a first conformation which is a straight wire. Upon the passage of electrical current, this straight wire may assume a second conformation which is an inverted conical spiral of preset maximal diameter.

For stent placement, the deployment segment of the delivery catheter may be placed over the shaft of an ancillary means of expansion, such as a balloon catheter. This may be advantageous, as the delivery of stents may be improved (relative to placement over a guide wire) by the use of a more rigid and larger diameter shaft as a guiderail for advancing the stent deployment segment assembly into the desired position. The shuttle may be coaxial with the ancillary means of expansion over the entire length or over part of the length of the ancillary means of expansion.

ANCILLARY MEANS OF EXPANSION

The stent delivery system of the invention provides for an ancillary means of expanding the deployment segment of the shuttle. While means of expansion other than a balloon catheter are envisioned, such as, for example, a nitinol wire, the distal segment of which is made to become a coil of a predetermined diameter when placed within the expandable deployment segment of the shuttle and when a weak electrical current is passed through such a nitinol wire, this ancillary element will be exemplified by and referred to hereafter as a balloon catheter.

The balloon catheter may be fabricated from a variety of materials, including, but not limited to, polyethylene and nylon, which are the preferred materials for the placement of stents in blood vessels.

As described above with relation to the shuttle, the length and radial diameter of the balloon catheter may vary depending upon the vessel or similar structure into which the stent is to be placed. For example, the approximate length of a balloon catheter for placement of a stent into a coronary artery may be in the range of from 80 to 140 centimeters, and preferably from 90 to 125 centimeters, and the radial diameter of the catheter portion may be in the range of from 0.8 to 1.6 millimeters, and preferably from 0.9 to 1.3 millimeters.

The balloon portion of the balloon catheter may desirably be structured such that the balloon is capable of repeatedly and reliably advancing in unexpanded condition as well as in collapsed condition through the entire length of the shuttle, and in and out of the distal end of the shuttle. For example, in order to achieve these goals, the balloon may preferably be a non-compliant high-pressure balloon with longer tapered ends and a smaller refolded diameter as depicted in FIG. 10. Such a balloon may have an exaggerated gradual gentle shoulder, wherein the change from the diameter of the balloon shaft adjacent to the balloon membrane (to which the balloon membrane is tethered) to the diameter of the fully expanded balloon takes place over a relatively long distance. Upon deflation, such a balloon, even if it is a high-pressure balloon, may preferably collapse with its edges re-wrapped snugly on the shaft without heaping up. Most preferably, such a balloon maintains the diameter of the collapsed balloon (which consists of the collapsed balloon membrane and tapered catheter shaft) smaller than the more proximal shaft of the catheter.

The balloon in preferably fabricated from polyethylene or nylon. In a specific, nonlimiting example, where the balloon is to be used in a delivery system for stent placement in coronary arteries, the balloon may preferably reach, in an inflated state, a diameter ranging from 2.0 to 5.0 millimeters, and more preferably from 2.5 to 4.5 millimeters, and an internal pressure of from 0 to 20 atmospheres, and more preferably from 4 to 20 atmospheres. Such a balloon may preferably have a rated burst pressure of from 12 to 20 atmospheres.

METHODS OF STENT PLACEMENT

The following is a general description of a method for stent placement. Various modifications to this method may be required depending on the structure into which the stent is to be placed, and the needs of particular patients.

First, the vessel or similar structure for stenting may be identified, and a path for the stent delivery system may be established. In the case of a blood vessel, a guiding catheter and a guide wire may be inserted.

Then, a shuttle with an expandable stent mechanically or by other means attached onto the deployment segment in contracted condition may be mounted coaxially over the shaft of a balloon catheter outside the patient in either over-the-catheter or monorail manner depending on the type of shuttle embodiment. The distal end of the balloon catheter becomes the distal tip of such shuttle-balloon catheter assembly.

Next, the shuttle-balloon catheter assembly may be inserted into the guiding catheter over the guide wire.

Where an embolic filter is used, the filter, in a collapsed state, may be advanced out of the guiding catheter distal to the obstructed region while the remainder of the shuttle is retained inside the guiding catheter by the application of traction on the proximal ends of the shuttle kept outside the patient. The filter may then be expanded by an intrinsic or ancillary mechanism (see supra).

Next, while the shuttle is retained on the shaft of the balloon catheter inside the guiding catheter by application of traction on its proximal end kept outside the patient, the means of expansion (e.g., balloon) may be positioned within the obstruction, expanded to predilate the region prior to stent placement (see FIG. 2), and then deflated and advanced distal to the obstruction. In certain circumstances, for example where an adequate passageway for the deployment segment of the shuttle already exists, predilatation may not be necessary. In such circumstances, the unexpanded balloon catheter may be advanced distal to the obstruction.

The stent, carried on the deployment segment of the shuttle, may then be moved into the desired position within (and preferably extending over) the obstruction, as shown in FIG. 3, while the position of the balloon catheter in the coronary artery is maintained by application of traction on its proximal end kept outside the patient. Radiopaque markers defining the location of the stent on the catheter may aid in stent positioning.

The deflated balloon may be withdrawn into the deployment segment, as shown in FIG. 4. In certain specific embodiments of the invention, this withdrawal may be facilitated by an alterable distal tip of the shuttle, for example, wherein the tip is constructed of a thermal memory alloy such as nitinol, and a weak electrical current may be used to create a wider aperture to facilitate withdrawal of the balloon.

Next, the balloon may be inflated to deploy the stent, as shown in FIG. 5. Where the stent is a self-expanding stent, expansion of the deployment segment creates a structural change that releases the constrained stent; for example, central expansion may release the stent from peripherally located sleeves which overlap the edges of the stent (see FIG. 7). Regions of the vessel on either side of the stent would tend to be protected by the relatively less expandable flanks on either side of the expandable portion of the deployment segment. In specific, nonlimiting embodiments of the invention, pharmaceutical substances may be released by expansion of the deployment segment.

Following deployment, the balloon may be deflated. If multiple stents are to be placed, pre-dilatation, repositioning, and deployment steps may be repeated. Otherwise, the entire stent delivery assembly may be withdrawn from the patient.

In a specific, non-limiting embodiment of the invention, where a Palmaz-Schatz stent is to be placed in a coronary artery of a subject, the following method may be used.

The ostium of the target coronary artery may be engaged with a 7F (2.33 millimeters) or larger external diameter guiding catheter with an internal diameter of not less than 2.0 millimeters. The target lesion in the target coronary artery may then be crossed with a guidewire compatible with the balloon catheter intended to be used for the procedure. The distal tip of the guide wire may be positioned as distally as possible in the target coronary artery. Typically, the guide wire with the stiffest shaft and of the largest diameter compatible with the balloon catheter intended to be used for the procedure may be used.

Then, a shuttle with a Palmaz-Schatz stent mechanically (or by other means) attached onto the deployment segment in contracted condition may be mounted coaxially over the shaft of a balloon catheter outside the patient in either over-the-catheter or monorail manner depending on the type of shuttle embodiment. The distal end of the balloon catheter becomes the distal tip of the shuttle-balloon catheter assembly. The balloon catheter compatible with the guide wire placed inside the target coronary artery may be used. The balloon catheter may be selected so that its expanded diameter is appropriate for the intended treatment site in the target vessel; typically, its diameter may be slightly greater than that of the target vessel immediately adjacent to the intended site of stent implantation.

Next, the shuttle-balloon catheter assembly may be inserted into the guiding catheter over the guide wire.

Next, while the shuttle is retained on the shaft of the balloon catheter inside the guiding catheter by application of traction on its proximal end kept outside the patient, the balloon segment of the balloon catheter may be positioned within the obstruction, expanded to 2 to 20 atmospheres for 15 to 300 seconds to predilate the region prior to stent placement (see FIG. 2), and then deflated and advanced distal to the obstruction. In certain circumstances, for example where an adequate passageway for the deployment segment of the stent delivery catheter already exists, pre-dilation may not be necessary. In such circumstances, the unexpanded balloon catheter may be advanced distal to the obstruction.

The Palmaz-Schatz stent, carried on the deployment segment of the shuttle, may then be moved into the desired position within (and preferably extending over) the obstruction, as shown in FIG. 3, while the position of the balloon catheter in the coronary artery is maintained by application of traction on its proximal end kept outside the patient. Radiopaque markers defining the location of the stent on the catheter may aid in stent positioning.

The deflated balloon may be withdrawn into the deployment segment, as shown in FIG. 4. In certain specific embodiments of the invention, this withdrawal may be facilitated by an alterable distal tip of the stent delivery catheter, for example, wherein the tip is constructed of a thermal memory alloy such as nitinol, and a weak electrical current may be used to create a wider aperture to facilitate withdrawal of the balloon.

Next, the balloon may be inflated to 6 to 20 atmospheres for 15 to 300 seconds to deploy the stent, as shown in FIG. 5. Regions of the vessel on either side of the stent would tend to be protected by the relatively less expandable flanks on either side of the expandable portion of the deployment segment. In specific, non-limiting embodiments of the invention, pharmaceutical substances may be released by expansion of the deployment segment.

Following deployment, the balloon may be deflated. If multiple Palmaz-Schatz stents are to be placed, pre-dilatation, repositioning, and deployment steps may be repeated. Otherwise, the entire stent delivery assembly may be withdrawn from the patient.

Various publications are cited herein, which are hereby incorporated by reference in their entireties.

What is claimed is:

1. A shuttle for delivering a stent in a patient comprising a tubular catheter having a proximal end and a distal end and having, at the distal end of the tubular catheter, a deployment segment, wherein the deployment segment comprises an expandable portion flanked, on both sides, by reenforced regions that are less expandable than the expandable portion, such that the deployment segment is capable of being expanded by means of a separate balloon catheter to deliver the stent in a desired location in the patient.

2. The shuttle of claim 1, wherein a stent is mounted on the deployment segment.

3. The shuttle of claim 2, wherein the stent is a self-expanding stent.

4. The shuttle of claim 2, wherein the stent is a non-self-expanding stent.

5. The shuttle of claim 4, wherein the stent is a Palmaz-Schatz stent.

6. The shuttle of claim 1, further comprising an embolic filter attached to the distal end of the tubular catheter.

7. The shuttle of claim 1, wherein the deployment segment comprises a pharmaceutical substance in releasable form.

8. A stent delivery system comprising
   (a) a shuttle for delivering a stent in a patient comprising a tubular catheter having a proximal end and a distal end and having, at the distal end of the tubular catheter, a deployment segment wherein the deployment segment comprises an expandable portion flanked, on both sides, by reenforced regions that are less expandable than the expandable portion;
   (b) a stent mounted on the expandable portion of the deployment segment; and
   (c) a balloon catheter having a shaft and comprising a balloon at its distal end;
   wherein the deployment segment is capable of being passed over the shaft of the balloon catheter and its expandable portion may be expanded by inflation of the balloon to deliver the stent in a desired location in the patient.

9. The stent delivery system of claim 8, further comprising an embolic filter attached to the distal end of the tubular catheter.

10. A method for placing a stent in a vasel of a patient wherein the vessel contains an obstruction, comprising
    (i) introducing a balloon catheter, having a shaft and comprising a balloon at its distal end, into the vessel such that the balloon is within the obstruction;
    (ii) inflating the balloon so as to dilate the obstruction;
    (iii) deflating the balloon;
    (iv) advancing the balloon distal to the obstruction;
    (v) passing a shuttle, comprising a tubular catheter having a proximal end and a distal end and having, at the distal end of the tubular catheter, a deployment segment wherein the deployment segment comprises an expandable portion flanked, on both sides, by reenforced regions that are less expandable than the expandable portion, and wherein a stent is mounted on the expandable portion of the deployment segment, over the balloon catheter, such that the stent is positioned within the dilated obstruction;
    (vi) withdrawing the deflated balloon into the shuttle such that the balloon lies within the deployment segment;
    (vii) inflating the balloon, thereby expanding the expandable portion of the deployment segment and delivering the stent within the dilated obstruction; and
    (viii) withdrawing the shuttle and the balloon catheter from the patient.

* * * * *